US00PP31073P2

(12) United States Plant Patent
Lim

(10) Patent No.: US PP31,073 P2
(45) Date of Patent: Nov. 19, 2019

(54) FLORIBUNDA ROSE PLANT NAMED 'ALTMINE'

(50) Latin Name: *Rosa hybrida*
Varietal Denomination: ALTmine

(71) Applicant: Altman Specialty Plants, Inc, Vista, CA (US)

(72) Inventor: Peter Lim, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/350,555

(22) Filed: Nov. 30, 2018

(51) Int. Cl.
*A01H 5/02* (2018.01)
*A01H 6/74* (2018.01)

(52) U.S. Cl.
USPC ..... Plt./145
CPC ..... *A01H 6/74* (2018.05)

(58) Field of Classification Search
USPC ..... Plt./145
CPC ..... A01H 5/0222
See application file for complete search history.

*Primary Examiner* — Kent L Bell
(74) *Attorney, Agent, or Firm* — Cassandra Bright

(57) ABSTRACT

A new and distinct floribunda *Rosa* cultivar named 'ALTmine' is disclosed, characterized by distinctive fully double yellow flowers with a sweet, spicy fragrance. Plants are vigorous and foliage glossy. The new variety is a *Rosa*, normally produced as an outdoor garden or container plant.

1 Drawing Sheet

Latin name of the genus and species: *Rosa hybrida.*
Variety denomination: 'ALTmine'.

BACKGROUND OF THE INVENTION

The new *Rosa* cultivar is a product of a planned breeding program conducted by the inventor, Peter Ping Lim. The objective of the breeding program was to produce vigorous new garden floribunda rose varieties for ornamental commercial applications. The cross resulting in this new variety was made during May of 2012.

The seed parent is the unpatented variety *Rosa* 'BAIine', U.S. Plant Pat. No. 16,659. The pollen parent is the variety *Rosa* 'WEKvossutono', U.S. Plant Pat. No. 18,473. The new variety was selected in 2013 by the inventor in a group of seedlings resulting from the 2012 crossing, in a nursery in Vista, Calif.

At the time of this filing plants of 'ALTmine' have not been publicly released. The first sale is scheduled for March of 2019 in the United States. Information about the new variety was published in *Nursery Management* magazine May of 2018. This publication, however, was not accompanied by any public access to plant material.

Asexual reproduction of the new cultivar was performed by vegetative cuttings. This was first performed at a research greenhouse in Vista, Calif. in June 2013 and has shown that the unique features of this cultivar are stable and reproduced true to type in more than 5 successive generations.

SUMMARY OF THE INVENTION

The cultivar 'ALTmine' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTmine' These characteristics in combination distinguish 'ALTmine' as a new and distinct *Rosa* cultivar:

1. Vigorous floribunda type plants.
2. Bright yellow, fully double flowers.
3. Glossy foliage.
4. Sweet spicy fragrance.

Plants of the new cultivar 'ALTmine' are similar to plants of the seed parent, in most horticultural characteristics, however, plants of the new cultivar 'ALTmine' differ in the following:

1. Petal color is different.
2. Much darker, glossier foliage.

Plants of the new cultivar 'ALTmine' are similar to plants of the pollen parent in most horticultural characteristics, however, plants of the new cultivar 'ALTmine' differs in the following;

1. Petal color is different.
2. Petal size is smaller than pollen parent.
3. Much darker, glossier foliage.

COMMERCIAL COMPARISON

Plants of the new cultivar 'ALTmine' can be compared to the commercial variety *Rosa* 'RADSUNNY' U.S. Plant Pat. No. 18,562. These varieties are similar in most horticultural characteristics, however 'ALTmine' differs in the following:

1. The new variety has more petals per flower.
2. Triploid Floribunda.
3. Petals of this comparator fade to white under summer heat, petals of the new variety maintain a yellow color in the heat.
4. This comparator has a taller plant size.
5. This comparator is less fragrant than the new variety.

Plants of the new cultivar 'ALTmine' can also be compared to the commercial variety *Rosa* 'Easy Going', U.S.

Plant Pat. No. 10,478. These varieties are similar in most horticultural characteristics, however 'ALTmine' differs in the following:

1. Petals of this comparator have an apricot colored blush not found in the new variety.
2. This comparator has a more clustered, tight inflorescence.
3. This comparator has more thorns, and harder thorns than the new variety.
4. This comparator has a more upright habit than the new variety.
5. This comparator is less fragrant than the new variety.

BRIEF DESCRIPTION OF THE PHOTOGRAPH

The accompanying photograph illustrates in full color a close up of an individual flower. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ALTmine' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTmine'.

Market classification: Floribunda.

PROPAGATION

Time to initiate roots: About 15 days at approximately 20° C.

Time to produce a rooted cutting: About 35 days at approximately 20° C.

Age of plant described: Approximately 2 years.

Growth habit: Compact spreading.

Container size: 2 gallon.

Height: 30 cm.

Plant spread: 47 cm.

Rootstock: Own root.

Growth rate: Moderate.

Branching characteristics: Sympodial branching.

Length of primary lateral branches: 10 to 13 cm.

Diameter of lateral branches: Approximately 5 mm.

Quantity branches: About 5 main branches, 8 to 10 lateral branches per main branch.

Branches-young wood:

*Diameter.*—3 to 5 mm.

*Texture.*—Glabrous.

*Approximately density/quantity of thorns.*—Approximately 3 per linear cm.

*Color.*—Near RHS Green 138A.

Branches-old wood:

*Diameter.*—1.5 to 2.0 cm.

*Color.*—Near RHS Greyed-Green 197B.

*Texture.*—Rough thick woody striations.

*Thorns.*—

*Approximately density/quantity of thorns.*—3 to 5 per linear cm.

*Color of thorns.*—Immature: RHS Yellow-Green 153D. Mature: Near RHS Greyed-Orange 166B.

*Shape.*—Deltoid, moderately hooked.

*Height.*—Average 5 mm.

*Diameter.*—Base near 2 mm. Tip near 0.2 cm.

FOLIAGE

Leaf:

*Arrangement.*—Alternate and compound.

*Quantity.*—Average 5 to 9 per main branch.

*Internode.*—Average range 1.3 to 4.0 cm.

*Average length.*—Approximately 9.0 cm.

*Average width.*—Approximately 6.5 cm.

Rachis:

*Average length.*—Approximately 5 cm.

*Average diameter.*—Approximately 0.2 cm.

*Color.*—Near RHS Green 138A.

*Texture.*—Glabrous all surfaces.

Leaflet:

*Quantity.*—5 per leaf.

*Average length.*—Approximately 4.0 cm.

*Average width.*—Approximately 3.0 cm.

*Shape of blade.*—Ovate.

*Apex.*—Acute.

*Base.*—Rounded.

*Margin.*—Serrate.

*Appearance of top surface.*—Very glossy.

*Appearance of bottom surface.*—Matte.

*Texture of top surface.*—Glabrous.

*Texture of bottom surface.*—Glabrous.

*Color.*—Young foliage upper side: Near RHS Yellow-Green 147B, flushed N186C. Young foliage under side: Near RHS Yellow-Green 148B, flushed 187B, veins 148B. Mature foliage upper side: Near RHS Green 137A. Mature foliage under side: Near RHS Green 138A.

*Venation.*—Type: Reticulate. Venation color upper side: Near RHS Green 137A. Venation color under side: Near RHS Green 138C.

Petiole:

*Average length.*—Approximately 2.0 cm.

*Average diameter.*—Approximately 0.2 cm.

*Color.*—Near RHS Green 137C.

*Texture.*—Glabrous.

FLOWER

Natural flowering season: Spring until Autumn.

Inflorescence type and habit: Single occurring, fully double rotate flowers.

Rate of flower opening: Approximately 4 days from bud to fully opened flower.

Flower longevity on plant: 10 to 14 days, after fully opened.

Quantity of flowers: 8 to 10 fully opened flowers and buds.

Flower size:

*Diameter.*—Approximately 7 cm.

*Height.*—Approximately 3 cm.

Peduncle:

*Length.*—3.5 cm.

*Diameter.*—0.35 cm.

*Color.*—Near RHS Green 143B.

Petals:

*Petal arrangement*.—Multiple rotate, overlapping whorls.

*Petal quantity*.—Approximately 40 to 60.

*Length*.—4 cm.

*Width*.—4 cm.

*Shape*.—Somewhat broad ovate.

*Margin*.—Entire.

*Apex*.—Rounded, sometimes notched with age.

*Base*.—Broad attenuate.

*Texture*.—Glabrous all surfaces.

Color:

*Petals*.—When opening: Upper surface: Near RHS Yellow 13A. Lower surface: Near RHS Yellow 13A. Fully opened: Upper surface: Near RHS Yellow 6C. Lower surface: Near RHS Yellow 6C. Fading: Upper surface: Near RHS Yellow 6C. Lower surface: Near RHS Yellow 6D.

Bud:

*Shape*.—Ovate.

*Length*.—Approximately 2 cm.

*Diameter*.—Approximately 1.5 cm.

*Color*.—Near RHS Yellow 6C.

Sepals:

*Quantity*.—5.

*Length*.—1.5 to 2 cm.

*Width*.—1.0 cm.

*Shape*.—Deltoid.

*Apex*.—Apiculate.

*Margin*.—Entire.

*Color*.—Interior Surface: Near RHS Green 138C. Exterior Surface: Near RHS Green 138B.

*Texture*.—Densely and minutely pubescent upper and lower surfaces.

*Receptacle*.—Length: 1.0 cm. Width: 1.4 cm. Shape: Flattened dome. Color: Near RHS Green 138B.

*Fragrance*.—Sweet, spicy fragrance.

REPRODUCTIVE ORGANS

Stamens:

*Quantity*.—Approximately 50 to 70.

*Filament length*.—Approximately 0.4 cm.

*Filament color*.—Near RHS Yellow 6C.

Anthers:

*Length*.—0.2 cm.

*Shape*.—Narrow globular.

*Color*.—Near RHS Yellow 6C.

*Pollen*.—Color: RHS Greyed-Orange N170A. Quantity: Scant.

Pistil:

*Length*.—Approximately 1 cm.

*Style*.—Length: Approximately 0.4 cm. Color: Near RHS Yellow 2D.

*Stigma*.—Shape: Linear. Color: Near RHS Yellow 2D. Ovary color: Near RHS Green 138B. Ovary shape: Oblong. Ovary length: Average 0.4 cm. Ovary diameter: Average 0.2 cm.

OTHER CHARACTERISTICS

Seeds and fruits: Not observed.

Disease/pest resistance: Good overall disease resistance to normal pests and diseases typical of garden roses.

What is claimed is:

1. A new and distinct floribunda *Rosa* plant named 'ALTmine' as herein illustrated and described.

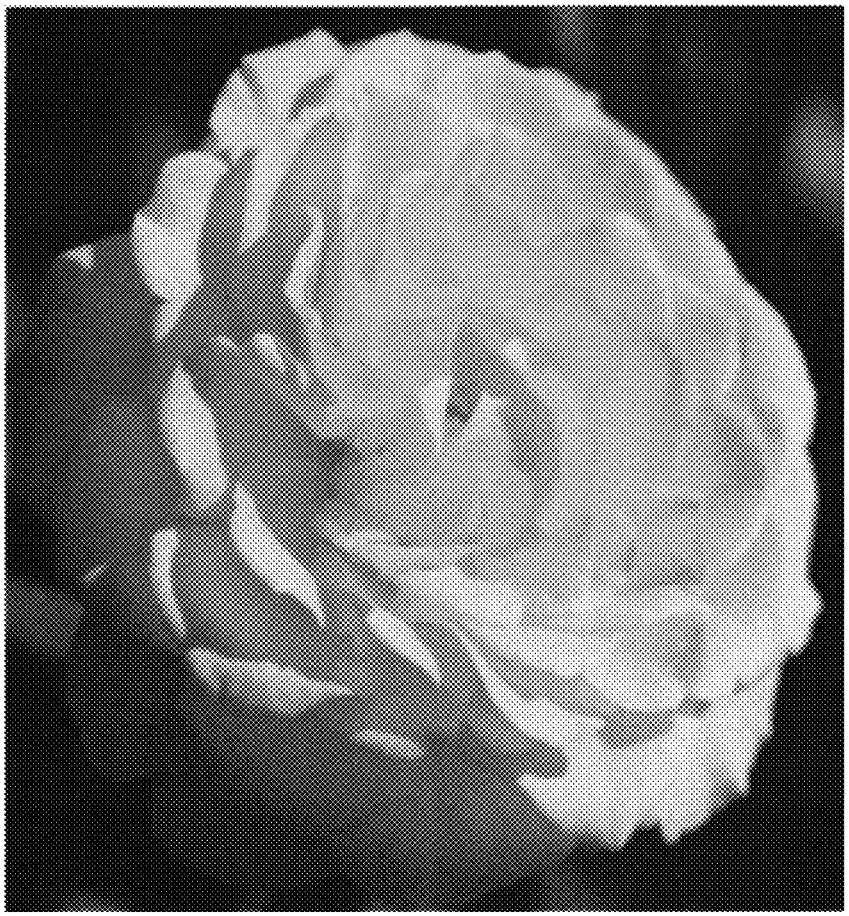

* * * * *